United States Patent [19]
Alber et al.

[11] Patent Number: 5,928,636
[45] Date of Patent: Jul. 27, 1999

[54] USE OF IL-12 AND IFNα FOR THE TREATMENT OF INFECTIOUS DISEASES

[75] Inventors: Gottfried Alber, Leipzig, Germany; Jacqueline Anne Carr, Ware, United Kingdom; Frank Albert Mattner, Mailand, Italy; Michael John Mulqueen, Rochford, United Kingdom; Kathrin Palmer, Münchenstein, Switzerland; Jane Andre Louise Rogerson, St. Albans, United Kingdom

[73] Assignee: Hoffmann-La Roche Inc., Nutley, N.J.

[21] Appl. No.: 08/845,973

[22] Filed: Apr. 30, 1997

[30] Foreign Application Priority Data

May 13, 1996 [GB] United Kingdom ............ 9609932

[51] Int. Cl.$^6$ .................. A61K 38/20; A61K 38/21
[52] U.S. Cl. .................. 424/85.2; 424/85.7; 514/2; 514/8; 514/885; 514/895
[58] Field of Search ............. 424/85.1, 85.2, 424/85.4, 85.7; 514/2, 8, 12, 885, 895

[56] References Cited

U.S. PATENT DOCUMENTS

| | | | |
|---|---|---|---|
| 5,457,038 | 10/1995 | Trinchieri et al. | 435/69.52 |
| 5,569,454 | 10/1996 | Trinchieri et al. | 424/85.2 |
| 5,648,072 | 7/1997 | Trinchieri et al. | 424/85.2 |
| 5,648,467 | 7/1997 | Trinchieri et al. | 536/351 |

FOREIGN PATENT DOCUMENTS

| | | |
|---|---|---|
| 2180193 | 12/1996 | Canada. |
| 032 134 | 7/1981 | European Pat. Off.. |
| 043 980 | 1/1982 | European Pat. Off.. |
| 174 143 | 3/1986 | European Pat. Off.. |
| 211 148 | 2/1987 | European Pat. Off.. |
| 433 827 | 6/1991 | European Pat. Off.. |
| 90/05147 | 5/1990 | WIPO. |
| 92/05256 | 4/1992 | WIPO. |

OTHER PUBLICATIONS

Johnston et al., Science, vol. 260, pp. 1286–1293, 1993.
Fahey et al. Clin. Enp. Immunol. vol. 88, pp. 1–5, 1992.
Arai et al. Ann. Rev. Biochem. vol. 59, pp. 783–836, 1990.
Levy J. Microbiological Reviews, pp. 183–289, vol. 57, No. 1, 1993.
Carr, J.A. et al., Database Biosis, Biosciences Information Service, "Dual therapy with IL–12 and IFN—alpha provides a novel approach to the management of chronic viral disease." Antiviral Research 34(2) (1997) A65.
Chehimi, J., et al., Natural Killer (NK) Cell Stimulatory Factor Increases the Cytotoxic Activity of NK Cells from Both Healthy Donors and Human Immunodeficiency Virus–infected Patients, J. Exp. Med., 175, 789–796 (1992).
Rogerson, J., et al, Co–therapy with Suboptimal Doses of Interleukin–12 and Interferon–α Promotes Synergistic Protection against Herpes Virus Infection, Annals Of the New York Academy of Sciences, vol. 795, 354–356 (1996).

Lachgar, A. et al., Involvement of α–interferon in HIV–1 induced immunosuppression. A potential target for AIDS prophylaxis and treatment. Biomedicine & Pharmacotherapy, vol. 48, No. 2, 73–77, (1994).
Seder, R., et al., Interleukin 12 acts directly on CD4+ T cells to enhance priming for interferon γ production and diminishes interleukin 4 inhibition of such priming, Proc. Natl. Acad. Sci. USA, 90:10188–10192 (1993).
Stern, A., et al., Purification to homogeneity and partial characterization of cytotoxic lymphcoyte maturation factor from human B–lymphoblastoid cells, Proc. Natl. Acad. Sci. USA, 87:6808–6812 (1990).
Tripp, C., et al., Interleukin 12 and tumor necrosis factor α are costimulators of interferon γ production by natural killer cells in severe combined immunodeficiency mice with listeriosis, and interleukin 10 is a physiologic antagonist, Proc. Natl. Acad. Sci. USA, 90:3725–3729 (1993).
Wong, H., et al., Characterization of a Factor(s) which Synergizes with Recombinant Interleukin 2 in Promoting Allogeneic Human Cytolytic T–Lymphocyte Responses in Vitro, Cellular Immunology, 111:39–54 (1988).
Wu, C–Y., et al., IL–12 Induces the Production of IFN–γ by Neonatal Human CD4 T Cells, J. Immunol., 151:1938–1949 (1993).
Gray, P., et al., Expression of human immune interferon cDNA in E. coli and monkey cells, Nature, 295:503–508 (1982).
Nagata, S., et al., Synthesis in E. coli of a polypeptide with human leukocyte interferon activity, Nature, 284:316–320 (1980).
Chan, S., et al., Induction of Interferon γ Production by Natural Killer Cell Stimulatory Factor: Characterization of the Responder Cells and Synergy with Other Inducers, J. Exp. Med., 173:869–879 (1991).
Cavalieri, R., et al., Synthesis of human interferon by Xenopus laevis oocytes: Two structural genes for interferons in human cells, Proc. Natl. Acad. Sci. USA, 74:3287–3291 (1977).
Bloom, E.T., and J. Horvath, Cellular and Molecular Mechanisms of the IL–12–Induced Increase in Allospecific Murine Cytolytic T Cell Activity, J. Immunol., 152:4242–4254 (1994).

(List continued on next page.)

Primary Examiner—Prema Mertz
Attorney, Agent, or Firm—George W. Johnson; William H. Epstein; Briana C. Buchholz

[57] ABSTRACT

The present invention provides a combination of IL-12 and IFNα together with a pharmaceutically acceptable carrier useful for treatment and prophylaxis of infectious diseases, preferably chronic infectious diseases and more preferably viral infections, e.g. HSV, HIV, Hepatitis B, Hepatitis C, papilloma etc., bacterial infections, e.g. tuberculosis, salmonellosis, listeriosis, etc., and parasite infections, e.g. malaria, leishmaniasis, and schistosomiasis. These compositions are characterized by the synergistic interaction of IL-12 and IFNα. The present invention also provides the use of the above combination for the treatment and prophylaxis of infectious diseases.

42 Claims, No Drawings

OTHER PUBLICATIONS

Brunda, M., et al., Antitumor and Antimetastatic Activity of Interleukin 12 against Murine Tumors, J. Exp. Med., 178:1223–1230 (1993).

Cesano, A., et al., Cellular and Molecular Mechanisms of Activation of MHC Nonrestricted Cytotoxic Cells by IL–12, J. Immunol., 151:2943–2957 (1993).

Chan, S., et al., Mechanisms of IFN–γ Induction by Natural Killer Cell Stimulatory Factor (NKSF/IL–12), Role of Transcription and mRNA Stability in the Synergistic Interaction between NKSF and IL–2, J. Immunol., 148:92–98 (1992).

Familletti, P., et al., Production of High Levels of Human Leukocyte Interferon from a Continuous Human Myeloblast Cell Culture, Antimicrob. Agents & Chemother., 20:5–9 (1981).

Goeddel, D., et al., The Structure of eight distinct cloned human leukocyte interferon cDNAs, Nature, 290:20–26 (1981).

Manetti, R., et al., Interleukin 12 Induces Stable Priming for Interferon γ (IFN–γ) Production During Differentiation of Human T Helper (Th) Cells and Transient IFN–γ Production in Established Th2 Cell Clones, J. Exp. Med., 179:1273–1283 (1994).

Nastala, C., et al., Recombinant IL–12 Administration Induces Tumor Regression in Association with IFN–γ Production, The Journal of Immunology, vol. 153:1697–1706 (1994).

Kobayashi, M., et al., Identification and Purification of Natural Killer Cell Stimulatory Factor (NKSF), A Cytokine with Multiple Biologic Effects on Human Lymphocytes, J. Exp. Med., 170:827–845 (1989).

Orange, J., et al., Effects of IL–12 on the Response and Susceptibility to Experimental Viral Infections, J. Immunol., 152:1253–1264 (1994).

Pestka, S., et al., Interferons And Their Actions, Ann. Rev. Biochem., 56: 727–77 (1987).

USE OF IL-12 AND IFNα FOR THE TREATMENT OF INFECTIOUS DISEASES

The present invention relates to the field of prevention and treatment of infectious diseases using a combination of Interleukin-12 (IL-12) and Interferon- α (IFNα). This combination is especially useful for the prophylaxis and treatment of chronic infectious diseases, e.g. viral infections, intracellular bacterial infections and parasite infections.

BACKGROUND OF THE INVENTION

Interleukin 12 (IL-12), formerly called natural killer cell stimulatory factor (Kobayashi et al. (1989) J. Exp. Med. 170, 827–845) and cytotoxic lymphocyte maturation factor (Stern et al. (1990) Proc. Natl. Acad. Sci. U.S.A. 87, 6808–6812), has potent anti-tumor and antimetastatic activity in several murine tumor models (Brunda et al. (1993) J. Exp. Med. 178, 1223–1230; Nastala et al. (1994) J. Immunol. 153, 1697–1706). Although the mechanism through which IL-12 exerts its anti-tumor effects is not completely understood, it has been shown that IL-12 induces a variety of biological effects on natural killer and T cells in vitro (Manetti et al. (1994) J. Exp. Med. 179, 1273–1283; Wu et al. (1993) J. Immunol. 151, 1938–1949; Tripp et al. (1993) Proc. Natl. Acad. Sci. U.S.A. 90, 3725–3729; Seder et al. (1993) Proc. Natl. Acad. Sci. U.S.A. 90, 10188–10192; Bloom et al. (1993) J. Immunol. 152, 4242–4254; Cesano et al. (1993) J. Immunol. 151, 2943–2957; Chan et al. (1992) J. Immunol. 148, 92–98). Activation of cytotoxic T lymphocytes by IL-12 is considered crucial in its anti-tumor activity (Brunda et al. (1993) J. Exp. Med. 178, 1223–1230). The IL-12 anti-tumor effect is partially maintained in severe combined immune deficient (SCID) and nude mice, both of which are T cell-deficient, and in CD8*-depleted euthymic mice (Brunda et al. (1993) J. Exp. Med. 178, 1223–1230; O'Toole et al. (1993) J. Immunol. 150, 294A). These results demonstrate that IL-12 has potent in vivo antitumor and antimethastatic effects against murine tumors and demonstrate as well the critical role of $CD8^+$ T cells in mediating the antitumor effects against subcutaneous tumors.

Interferons (IFNs) are naturally occurring proteins which have antiviral, antiproliferative and immunoregulatory activity. Four distinct classes of interferons are known to exist in humans (Pestka et al. (1987) Ann. Rev. Biochem. 56, 727–777 and Emanuel & Pestka (1993) J. Biol. Chem. 268, 12565–12569). The IFNα family represents the predominant class of IFNs produced by stimulated peripheral blood leukocytes (Pestka et al., loc. cit.; Havell et al. (1975) Proc. Natl. Acad. Sci. U.S.A. 72, 2185–2187; Cavalieri et al. (1977) Proc. Natl. Acad. Sci. U.S.A. 74, 3287–3291), and lymphoblastoid and myeloblastoid cell lines (Familletti et al. (1981) Antimicrob. Agents. Chemother. 20, 5–9). The antiviral effect of IFNα is achieved not by a direct influence on the viruses themselves, but by an activity on their target cells in the sense of a protection against the virus infection. The interferons can exert effects on cancer tumors and can influence the immune system of the body on that, for example, they activate macrophages and NK cells and intensify the expression of various immunologically significant constituents of the cell membrane. Details of the preparation of interferon-cDNA and the direct expression thereof, especially in *E. coli*, have been the subject of many publications. Thus, for example, the preparation of recombinant interferons is known, for example, from Nature 295 (1982), 503–508, Nature 284 (1980), 316–320, Nature 290 (1981), 20–26, Nucleic Acids Res. 8 (1980), 4057–4074, as well as from European Patents Nos. 32134, 43980 and 211 148.

IFNα has proven to be effective in the treatment of viral infections, e.g. both Hepatitis B and Hepatitis C virus (HBV, HCV) infections, however a significant number of patients do not respond to this cytokine. The ability of IL-12 to promote both Th1 maturation and the enhancement of CTL and NK activity is likely to be critical for its ability to protect against disease in mouse models of viral infections (Orange et al. (1994) J. Immunol. 152, 1253–1264).

The present invention relates to the field of prevention and treatment of infectious diseases using IL-12 in combination with IFNα. Surprisingly, sub-optimal doses of IL-12 and IFNα promote effective protection in vitro and in vivo against infectious diseases, especially against viral and parasite infections and intracellular bacterial infections.

SUMMARY OF THE INVENTION

In accordance with the present invention, a combination of IL-12 and IFNα together with a pharmaceutically acceptable carrier is provided which is effective in treatment and prophylaxis of infectious diseases, preferably chronic infectious diseases and more preferably viral infections, e.g. Herpes (HSV), HIV, Hepatitis B, Hepatitis C, papilloma etc., intracellular bacterial infections, e.g. tuberculosis, salmonellosis, listeriosis, etc., and parasite infections, e.g. malaria, leishmaniasis, schistosomiasis. These compositions are characterized by the synergistic interaction of IL-12 and IFNα. They are easily administered by different routes including parenteral and can be given in dosages that are safe and sufficient to treat or prevent infectious diseases. The above pharmaceutical compositions may contain additional compounds useful for the treatment of infectious diseases. The present invention also provides the use of the above compounds for the manufacture of medicaments for the treatment and prophylaxis of infectious diseases mentioned above.

DETAILED DESCRIPTION OF THE INVENTION

The present invention provides the use of IL-12 and IFNα for the preparation of medicaments for the treatment of infectious diseases, especially chronic infectious diseases. These infectious diseases are caused by transfer of viral, bacterial, parasite and of other microorganisms. A particular use of the combination of IL-12 and IFNα according to the present invention is the preparation of medicaments for the prophylaxis and treatment of viral diseases, preferably chronic viral infections, e.g. hepatitis, herpes, papilloma, or human immunodeficiency virus infections. A further embodiment of the present invention comprises the use of the above compounds for the prophylaxis and treatment of bacterial infectious diseases, preferably intracellular bacterial infectious diseases, e.g. tuberculosis, salmonellosis or listerosis. The present invention relates also to the use of the above compounds for the treatment of parasite infections. Parasite infectious diseases comprise infectious diseases like malaria, leishmaniosis or schistomsomiasis.

In addition, the present invention relates also to the corresponding pharmaceutical compositions useful for the treatment of the above diseases. The pharmaceutical compositions are characterized in that they contain IL-12, IFNα and a pharmaceutically acceptable carrier. These compositions may contain one or more additional compounds useful for the prophylaxis and treatment of infectious diseases.

The results of the present invention indicate that suboptimal doses of IL-12 and IFNα can synergise to provide protection against infectious diseases, and this is mediated at least in part by IFNγ. Surprisingly, data from in vitro experimental work show increased production of IFNγ from spleen cells of IL-12/IFNα treated animals. Thus, an enhanced Th1 response to infectious diseases underlines the beneficial effects of IFNα/IL-12 combination therapy.

Data obtained from the in vitro Th1/Th2 differentiation system are supported by murine models of Herpes virus infection. Animals infected with HSV were dosed with cytokines as described in Experiment 2. Since IL-12 appeared to be less efficacious against HSV when dosed subcutaneously as opposed to intraperitoneally (Table 1), subcutaneous dosing of IL-12 was decided as the preferred route in these studies. Subtherapeutic doses of both IL-12 and IFNα were determined from dose response curves to systemic HSV-2 ($10^4$ pfu i.p) infection, these were determined to be 50 ng s.c and 1000 Units i.p respectively.

Co-administration of IL-12 and IFNα at subtherapeutic doses gives significantly greater ($p<0.001$) protection against systemic HSV-2 infection than either given alone (Table 1). The animals tested are also protected against subsequent re-infection of HSV-2. To examine the contribution of IFNγ to the protection induced by IL-12/IFNα cotherapy, a neutralizing antibody (XMG1.2) was administered throughout the course of the experiment. Depletion of IFNγ resulted in a reduced survival, although significant protection still occurred in the IL-12/IFNγ group. This suggests that at least part of the synergistic effect is through mechanisms other than IFNγ.

TABLE 1

Systemic Survival Data

| Treatment Group | Dose Level and Route | % Mortality on Day 20 |
| --- | --- | --- |
| Vehicle control | i.p or s.c | 94 ± 4 |
| IL-12 | 50 ng i.p | 30 ± 10 |
| IL-12 | 50 ng s.c | 88 ± 5 |
| IFNα | 1000 Units i.p | 74 ± 3 |
| IL-12 and IFNα | 50 ng s.c and 1000 Units i.p respectively | 22 ± 9 |

Female Balb/c mice were infected with $10^4$ or $10^5$ pfu HSV-2 (strain 333) by i.p infection. Animals were monitored until 20 days post infection for disease symptoms and death.

Studies in the zosteriform model of HSV-2 infection ($10^6$ pfu/10 μl i.d) indicate that animals given both IL-12 and IFNα have a reduced lesion score ($p<0.01$) and mortality compared to those given L-12 and IFNα alone (FIG. 7; Table 2). As described above, in vitro studies confirm IFNγ production in groups given both IL-12 and IFNα co-therapy.

TABLE 2

Zoster Survival Data

| Treatment Group | Dose and route | Lesion Score (AUC/d/mouse) | p value | % Mortality on Day 14 |
| --- | --- | --- | --- | --- |
| Vehicles |  | 1.6 |  | 54 |
| IL-12 | 50 ng s.c | 1.3 | N.S | 47 |
| IFNα | 1000 Units i.p | 1.5 | N.S | 73 |
| IL-12 + IFNα | 50 ng s.c + 1000 Units i.p | 1.0 | 0.01 | 27 |

Female Balb/c mice were infected as described and dosed with IL-12 and/or IFNα as indicated. They were monitored for skin lesions and deaths for 12–14 days post infection.

In summary, the results show that sub-optimal doses of IL-12 and IFNα together promoted effective protection in vitro and in vivo against infectious diseases. The studies indicate that enhanced survival may be correlated with an increase in Th1 induction, since spleen cells given co-therapy produced high levels of IFNγ, following in vitro stimulation.

The central role of IFNγ has also been shown in defense against intracellular bacteria (Listeria monocytogenes). Anti-IFNγ treatment prior to infection increases susceptibility, whereas rIFNγ increases resistance. One major function of IFNγ is the activation of macrophages for their microzidal activities, e.g. production of reactive oxidative intermediates. In addition, several findings have demonstrated the importance of IFNγ for the elimination of intracellular parasites (L. major) by infected hosts. The destruction of parasites by murine macrophages was shown to result from the IFNγ-induced production of nitric oxide by these cells.

Interleukin-12 may be prepared by methods known in the art, e.g. described in European Patent Application No. 433827, in International Patent Applications WO 9005147 and WO 9205256, in Kobayashi et al., J. Exp. Med. 170, 827–845 (1989) and Stern et al. (1990) Proc. Natl. Acad. Sci. U.S.A. 87, 6808–6812. Interleukin-12 may be produced by known conventional chemical synthesis, recombinant methods or may be purified from natural sources.

IFNα to be contained in the present composition may be those derived from any natural material (e.g., leukocytes, fibroblasts, lymphocytes) or material derived therefrom (e.g. cell lines), or those prepared with recombinant DNA technology. Details of the cloning of IFNα and the direct expression thereof, especially in E.coli, have been the subject of many publications. The preparation of recombinant IFNs is known, for example from Gray et al. (1982) Nature 295, 503–508, Goeddel et al. (1980) Nature 284, 316–320 and (1981, Nature 290, 20–26, and European Patent No. 174143. There are many types of IFNα such as IFNαI, IFNα2; and further their subtypes including but not limited to IFNα2A, IFNα2B, IFNα2C and IFNαII (also designated IFNα$_{II}$ or ω-IFN).

The terms "IL-12" and "IFNα" suitable for pharmaceutical compositions also comprise polypeptides similar to those of the purified and/or recombinant protein but which modifications are naturally provided or deliberately engineered, e.g. molecules containing inversions, deletions, insertions and modifications (such as pegylated forms of IFNα and/or IL-12) as well as any hybrid or consensus IL-12 or IFNα molecules obtainable from the aforementioned molecules.

Pharmaceutically acceptable formulations of IL-12 and IFNα in connection with this invention can be made using formulation methods known to those of ordinary skill in the art. These formulations can be administered by standard routes. In general, the formulations may be administered parenterally (e.g., intravenous, subcutaneous or intramuscular) with topical, transdermal, oral, or rectal routes also being contemplated In addition, the formulations may be incorporated into biodegradable polymers allowing for sustained release of IL-12 and IFNα, the polymers being implanted in the vicinity of where drug delivery is desired, for example, at the site of a tumor. The biodegradable polymers and their use are described, for example, in detail in Brem et al. (1991) J. Neurosurg. 74, 441–446. The dosage of IL-12 and IFNα will depend on the condition being treated, the particular compound, and other clinical factors such as weight and condition of the human or animal and the route of administration of IL-12. It is to be understood that the present invention has application for both human and veterinary use. For parenteral administration (preferably subcutaneous) to humans, a dosage of between approximately 1000 ng IL-12 to about 10 ng/kg body weight 1 to 3 times a week, preferably between approximately 300 ng to about 30 ng/kg 1 to 3 times a week is generally sufficient. For IFNα a dosage of between approximately 50 μg to about 0.1 μg/kg body weight 1 to 3 times a week, preferably between approximately 15 μg to about 1 μg 1 to 3 times a week is generally sufficient. It will however be appreciated that the upper and lower limit given above can be exceeded when this is found to be indicated.

The formulations include those suitable for parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association IL-12 and IFNα and the pharmaceutical carrier (s) or excipient(s). In general, the formulations are prepared by uniformly and intimately bringing into association the IL-12 and IFNα with liquid carriers. Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, seated ampoules and vials, and may be stored in a freeze-dried (lyophilized) conditions requiring only the addition of the sterile liquid carrier, for example, water for injections, immediately prior to use.

Preferred unit dosage formulations are those containing a daily dose or unit, daily sub-dose, as herein above recited, or an appropriate fraction thereof, of the administered ingredient.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talk or stearic acid or salts thereof.

Suitable excipients for use with soft gelatine capsules include for example vegetable oils, waxes, fats, semi-solid or liquid polyols etc. For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols. The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

The following Examples are intended to illustrate details of the invention, without thereby limiting it in any manner.

EXAMPLES

Example 1

In Vitro maturation of Th1 cells

Experiments regarding the in vitro maturation of Th1 cells were done as follows a) Murine spleen cells 8–10 weeks old female C57BL7/6 mice were used to prepare a single cell suspension of spleen cells in Hanks medium+1% FCS. Red cells were removed with Geys solution and preactivated cells by a Percoll gradient centrifugation according to standard methods (Cambier et al. (1987) Scand. J. Immunol. 27, 59).

b) CD4+ purification $10^7$ splenocytes per ml were incubated in Hanks medium, 10 μg/ml mAb anti-IA/IE (clone M5/114, Bhattacharya et al. (1981) J. Immunol. 127, 2488) and 10 μg/ml mAB anti-CD8 (clone 53-6.7, Ledbetter et al. (1979) Immunol. Rev. 47, 63) were added. After 30 minutes incubation on ice and washing (3x) the cells were resuspended at $5\times10^6$ cells/ml. 100 μl Magnetic Dyna Beads (Sheep anti Rat) were added and after 30 minutes rotation at 4° C. the target cells (bound to the beads) were removed with a magnet. The purity of CD4+ cells was more than 90%. These cells were resuspended in complete IMDM at $10^6$ cells/ml.

c) Activation of CD4+ cells 48 well cell culture plates were coated with mAb anti-CD3 (clone 2C11, Leo et al. (1987) PNAS 84, 1374) at 5 μg/ml). The plates were washed (3x) and 500 μl purified CD4+ cell suspension per well and cytokines (IL-12, IL-4, IFN-αA/D), native IFN-α) and their combinations were added. After incubation for 5 days at 37° C.+7.5% $CO_2$ the cells were washed (3x), resuspended in 700 μl medium, transferred to new anti-CD3-coated 96 well cell culture plate (200 μl per well) and incubated for 24–48 h. After collection of the cell culture supernatant IFNγ (IL-4, IL-10) were measured using commercially available lymphokine-specific ELISA tests.

Example 2

Herpes Simplex Virus-2 (HSV-2) infection

Murine model of Herpes Simplex Virus-2 (HSV-2) infections were used to investigate the efficacy of IFNα and IL-12 in the treatment of viral infections.

Female Balb/c mice (20–25 grams) were obtained from Harlan and dosed as follows: On the day of infection IFNα-A/D (1000 Units) was administered intraperitoneally 2 hours prior to, then 4 hours post infection. IL-12 (50 ng) was given subcutaneously 6 hours after infection, then IL-12 and/or IFNα was given daily for a further 4 days.

a) Systemic infection

Animals were infected with HSV-2 (strain 333) via the intraperitoneal route at a concentration of $10^5$ pfu/100 μl/mouse. They were dosed with cytokine as described above. A separate group of animals treated with both IL-12 and IFNα were given the interferon-γ depleting antibody (100 μg i.p.)XMG1.2, one day prior to infection then throughout the dosing period up until day 10.

b) Zosteriform infection

The left side of each mouse was shaved and depilated 24 hours before the skin directly above the spleen was scarified with needle and had 10 μl of virus containing $10^6$ pfu HSV-2 placed onto it. Animals were left to recover and dosed as previously described. Animals were monitored daily for mortality and where appropriate for lesion development until day 20 for systemic infection and day 14 for zoster. Mortality data from the studies were compared across groups using logrank analysis and data is displayed as survival curves and mean lesion score.

c) In vitro studies

Single cell suspension of drawing lymph nodes and spleens were obtained form all groups on day 7–10 post infection and cultured in complete RPMI+10% FCS at 37° C. for four days, stimulated with Con A. After 48 hrs supernatants from spleen cell were taken to look for IFNγ production, using commercially available ELISA kits.

We claim:

1. A pharmaceutical composition in unit dosage form for parenteral administration to a human patient said composition comprising:

Interleukin-12 in an amount from about 10 to about 1000 nanograms/kilogram of body weight of said human patient; and Interferon-α in an amount from about 0.1 to about 50 micrograms/kilogram of body weight of said human patient; together with a pharmaceutically acceptable carrier.

2. The composition of claim 1, wherein said amount of Interleukin-12 is from about 30 to about 300 nanograms/kilogram of body weight of said human patient.

3. The composition of claim 2, wherein said amount of Interferon-α is from about 1 to about 15 micrograms/kilogram of body weight of said human patient.

4. A method of treating a viral infection in a human patient in need of such treatment comprising administering to the patient a pharmaceutical composition comprising a therapeutically effective amount of Interleukin-12 for such treatment; and a therapeutically effective amount of Interferon-α for such treatment; together with a pharmaceutically acceptable carrier; wherein said viral infection is selected from the group consisting of herpes (HSV), hepatitis B, hepatitis C and papilloma.

5. The method of claim 4, wherein said amount of Interleukin-12 is from about 10 to about 1000 nanograms/kilogram of body weight of said human patient administered 1 to 3 times per week.

6. The method of claim 5, wherein said amount of Interferon-α is from about 0.1 to about 50 micrograms/kilogram of body weight of said human patient administered 1 to 3 times per week.

7. The method of claim 6, wherein said amount of Interleukin-12 is from about 30 to about 300 nanograms/kilogram of body weight of said human patient.

8. The method of claim 7, wherein amount of Interferon-α is from about 1 to about 15 micrograms/kilogram of body weight of said human patient.

9. A method of treating a bacterial infection in a human patient in need of such treatment comprising administering to the patient a pharmaceutical composition comprising a therapeutically effective amount of Interleukin-12 for such treatment; and a therapeutically effective amount of Interferon-α for such treatment; together with a pharmaceutically acceptable carrier.

10. The method of claim 9, wherein the bacterial infection is selected from the group consisting of tuberculosis, salmonellosis and listerosis.

11. The method of claim 9, wherein said amount of Interleukin-12 is from about 10 to about 1000 nanograms/kilogram of body weight of said human patient administered 1 to 3 times per week.

12. The method of claim 11, wherein said amount of Interferon-α is from about 0.1 to about 50 micrograms/kilogram of body weight of said human patient administered 1 to 3 times per week.

13. The method of claim 12, wherein said amount of Interleukin-12 is from about 30 to about 300 nanograms/kilogram of body weight of said human patient.

14. The method of claim 13, wherein said amount of Interferon-α is from about 1 to about 15 micrograms/kilogram of body weight of said human patient.

15. A method of treating a parasitic infection in a human patient in need of such treatment comprising administering to the patient a pharmaceutical composition comprising a therapeutically effective amount of Interleukin-12 for such treatment; and a therapeutically effective amount of Interferon-α for such treatment; together with a pharmaceutically acceptable carrier.

16. The method of claim 15, wherein the parasitic infection is selected from the group consisting of malaria, leishmaniosis and schistosomiasis.

17. The method of claim 15 wherein said amount of Interleukin-12 is from about 10 to about 1000 nanograms/kilogram of body weight of said human patient administered 1 to 3 times per week.

18. The method of claim 17, wherein said amount of Interferon-α is from about 0.1 to about 50 micrograms/kilogram of body weight of said human patient administered 1 to 3 times per week.

19. The method of claim 18, wherein said amount of Interleukin-12 is from about 30 to about 300 nanograms/kilogram of body weight of said human patient.

20. The method of claim 19 wherein said amount of Interferon-α is from about 1 to about 15 micrograms/kilogram of body weight of said human patient.

21. A method of preventing a viral infection in a human patient susceptible to viral infections comprising administering to the patient a pharmaceutical composition comprising: an amount of Interleukin-12 and an amount of Interferon-α, wherein said amounts of Interleukin-12 and Interferon-α are effective for preventing said viral infection in said patient; together with a pharmaceutically acceptable carrier; wherein said viral infection is selected from the group consisting of herpes (HSV), hepatitis B, hepatitis C and papilloma.

22. The method of claim 21, wherein said amount of Interleukin-12 is from about 10 to about 1000 nanograms/kilogram of body weight of said human patient administered 1 to 3 times per week.

23. The method of claim 22, wherein said amount of Interferon-α is from about 0.1 to about 50 micrograms/kilogram of body weight of said human patient administered 1 to 3 times per week.

24. The method of claim 23, wherein said amount of Interleukin-12 is from about 30 to about 300 micrograms/kilogram of body weight of said human patient.

25. The method of claim 24, wherein said amount of Interferon-α is from about 1 to about 15 micrograms/kilogram of body weight of said human patient.

26. A method of preventing a bacterial infection in a human patient in need of such treatment comprising administering to the patient a pharmaceutical composition comprising an amount of Interleukin-12 and an amount of Interferon-α, wherein said amounts of Interleukin-12 and Interferon-α are effective for preventing said bacterial infection in said patient; together with a pharmaceutically acceptable carrier.

27. The method of claim 26, wherein the bacterial infection is selected from the group consisting of tuberculosis, salmonellosis and listerosis.

28. The method of claim 26 wherein said amount of Interleukin-12 is from about 10 to about 1000 nanograms/kilogram of body weight of said human patient administered 1 to 3 times per week.

29. The method of claim 28, wherein said amount of Interferon-α is from about 0.1 to about 50 micrograms/kilogram of body weight of said human patient administered 1 to 3 times per week.

30. The method of claim 29, wherein said amount of Interleukin-12 is from about 30 to about 300 nanograms/kilogram of body weight of said human patient.

31. The method of claim 30, wherein said amount of Interferon-α is from about 1 to about 15 micrograms/kilogram of body weight of said human patient.

32. A method of preventing a parasitic infection in a human patient in need of such treatment comprising administering to the patient a pharmaceutical composition comprising an amount of Interleukin-12 and an amount of Interferon-α, wherein said amounts of Interleukin-12 and Interferon-α are effective for preventing said parasitic infection in said patient; together with a pharmaceutically acceptable carrier.

33. The method of claim 32, wherein the parasitic infection is selected from the group consisting of malaria, leishmaniosis and schistosomiasis.

34. The method of claim 32 wherein said amount of Interleukin-12 is from about 10 to about 1000 nanograms/kilogram of body weight of said human patient administered 1 to 3 times per week.

35. The method of claim 34, wherein said amount of Interferon-α is from about 0.1 to about 50 micrograms/kilogram of body weight of said human patient administered 1 to 3 times per week.

36. The method of claim 35, wherein said amount of Interleukin-12 is from about 30 to about 300 nanograms/kilogram of body weight of said human patient.

37. The method of claim 36, wherein said amount of Interferon-α is from about 1 to about 15 micrograms/kilogram of body weight of said human patient.

38. A method of stimulating T cells in a human patient infected with HIV comprising parenterally administering to the patient a pharmaceutical composition comprising a therapeutically effective amount of Interleukin-12; and a therapeutically effective amount of Interferon-α; together with a pharmaceutically acceptable carrier.

39. The method of claim 38, wherein said amount of Interleukin-12 for such treatment is from about 10 to about 1000 nanograms/kilogram of body weight of said human patient administered 1 to 3 times per week.

40. The method of claim 39, wherein said amount of Interferon-α is from about 0.1 to about 50 micrograms/kilogram of body weight of said human patient administered 1 to 3 times per week.

41. The method of claim 40, wherein said amount of Interleukin-12 is from about 30 to about 300 nanograms/kilogram of body weight of said human patient.

42. The method of claim 41, wherein said amount of Interferon-α is from about 1 to about 15 micrograms/kilogram of body weight of said human patient.

* * * * *